United States Patent [19]
Mathewson

[11] Patent Number: 5,597,577
[45] Date of Patent: Jan. 28, 1997

[54] WATER HYDRATABLE GEL-FILLED TEXTILE WRAP

[76] Inventor: Paul R. Mathewson, 7726 N. Buckboard Dr., Park City, Utah 84098

[21] Appl. No.: 492,398

[22] Filed: Jun. 19, 1995

[51] Int. Cl.$^6$ ..................................... A01N 25/34
[52] U.S. Cl. ............................ 424/402; 424/400
[58] Field of Search .................... 424/402, 400; 62/529, 530

[56] References Cited

U.S. PATENT DOCUMENTS

| | | | |
|---|---|---|---|
| 3,545,230 | 8/1968 | Morse | 62/530 |
| 4,055,188 | 10/1977 | Pelton | 128/402 |
| 4,910,978 | 3/1990 | Gordon | 62/530 |

Primary Examiner—Thurman K. Page
Assistant Examiner—Sharon Howard
Attorney, Agent, or Firm—Trask, Britt & Rossa

[57] ABSTRACT

A device for contributing a sense of cooling relief for the body, especially during physical recreational/leisure activities, is provided which makes use of a water-permeable textile envelope containing a particulate resinous gel-forming material. The particulate resinous material, when hydrated by emersion in water, forms a soft pliable gel-like substance. The cooling effect of this device is provided by the evaporation of water from the surface of the textile envelope. The fibers of the textile envelope, by capillary action, wick water from the interstitial spaces in the water hydrated gel material, carrying the water to the textile/air/skin interface. The water evaporating from that interface results in the evaporative cooling effect. The device is simple and convenient to use in virtually any location, indoors or out and can be utilized during a variety of recreational and leisure activities to mitigate the uncomfortable effects of heat.

7 Claims, 1 Drawing Sheet

WATER HYDRATABLE GEL-FILLED TEXTILE WRAP

BACKGROUND OF THE INVENTION

1) Field of the Invention

This invention relates to devices for cooling the body. Outdoor activities, particularly those participated in during the hotter times of the year, may lead to overheating, fatigue, excessive perspiring, and other related discomforts. It is known that application of water, cool compresses or other such cooling devices can relieve many of the symptoms related to overheating and help to prevent more serious consequences, such as heat stroke. The present invention addresses such concerns related to, or caused by, outdoor recreational or other leisure activities during warm weather where overheating is often a concern.

2) Description of Prior Art

All prior art in this particular field consists of relatively simple "home" remedies, the majority of which involve wrapping a moist piece of cloth, such as a towel, around the head or neck of the wearer to provide a cooling effect. While this approach may be moderately effective initially, the cooling effect is short-lived due to the rapid evaporation of the moisture from the towel or cloth.

Other cooling devices have been patented, all of which have been directed to therapeutic implementation using ice, and/or gels of various sorts which require freezing. Such devices are directed to the therapeutic cooling of certain body parts which have been injured in some way and require that the afflicted area be cooled to a significant degree. Therapeutic cooling requires that the temperature of the afflicted body area be significantly dropped (from about 35° C. to about 5° C.) for a period of at least fifteen minutes. This cooling usually relies on the high latent heat of fusion of water. Latent heat of fusion refers to the relatively large amount of heat required to melt ice. This results in the ability of the cooling device containing the frozen water (ice) to provide a relatively cold environment for a length of time sufficient to drop the temperature of the injured body part to the required extent to achieve therapeutic benefit. Such devices are disclosed in U.S. Pat. Nos. 3,545,230. 4,671,267, and 4,910,978.

Therapeutic cooling devices rely on the heat of fusion of water, in the form of ice, to provide the necessary cooling effect. The prior art discloses a number of configurations taking advantage of this property of water. One common feature of such devices is that they are comprised of a plastic or other vinyl-like envelope containing water or a water-containing gel-like material. In some inventions the envelope consists of plastic/vinyl envelope which is laminated to an outer material constructed from a woven or non-woven textile material. In any case, this envelope is essentially non-permeable to the free flow of water from inside the envelope to the outside.

The reliance of these therapeutic devices on the heat of fusion of water, that is the high heat capacity of the frozen water as ice, as well as the non-permeable nature of the container in which the water and/or gel is found, makes them unsuitable for the kind of recreational purpose for which the present invention is designed. The therapeutic devices must be exposed to very cold temperatures (below freezing) in order to lower the temperature of the water/gel sufficiently to provide a therapeutic benefit when used by the patient. Once exposed to the very warm conditions experienced in warm weather outdoor activities, the cooling effect rapidly dissipates and cannot be regenerated without returning the device to a freezer.

While several inventions have been patented disclosing devices for achieving a therapeutically significant drop in temperature at a specific location of an injury on the human body, these devices can be used only under restricted conditions and are wholly unsuited for cooling the body under conditions experienced while engaged in any of the many activities practiced out of doors in warm weather. Thus, a need exists for a simple, convenient device which can provide a sense of cooling relief to the wearer while engaged in any of the myriad forms of outdoor or indoor recreation.

SUMMARY OF THE INVENTION

The present invention has as its goal provision of a greatly improved means of providing cooling relief from the thermal effects of hot weather during physical activity. The detrimental results arising from exposure to the heat of the sun and of physical exertion during vigorous activities can be serious. The present invention diminishes such thermal effects by providing a mechanism through which the body may be cooled during such exposure.

The invention discloses a woven textile wrap which can be applied to various areas of the body which are sensitive to heat and cold. These areas include, but are not restricted to, the neck, head, face, wrists, shoulders, feet and back, among others. The textile wrap embodied in this invention comprises a textile-based envelope which contains a measured portion of a particulate gel-forming resinous material. The resinous material is capable of forming a gel when exposed to water. The dry resinous gel-forming material is capable of absorbing several hundred times its dry weight in water. The particulate resinous gel-forming material is contained within the textile wrap and is hydrated by immersing the textile wrap containing the particulate resinous gel-forming material in sufficient water. The non-hydrated resinous gel-forming material may have a particle size from about 5 microns to about 10,000 microns, the preferred size being in the range of about 200 to 2000 microns.

The textile wrap containing the hydrated and swollen resinous gel-forming material allows for the evaporation of water from its surface. The water slowly migrates from the internal interstices of the hydrated gel material to the surface of the textile wrap, where it evaporates. It is this evaporation of water rather than the melting of frozen water (ice) which provides the cooling effect through the phenomenon referred to as evaporative cooling. While it may be desirable to place the textile wrap containing the hydrated gel-forming material in a refrigerator to provide for additional cooling effect, cooling can and will be felt without prior refrigeration solely due to the evaporative cooling effect. Thus, while hydrated, the device can be used at virtually any location, outdoors or indoors, with consequent cooling effect. Moisture will be lost due to evaporation over time. Rejuvenation of the device can be accomplished simply by exposing the device to any source of water. If the device is allowed to dehydrate completely, the device returns to its original size and shape and weight which is significantly less in all respects compared to the hydrated form. Thus, the dehydrated device can be conveniently stored and transported when not in use.

The textile wrap containing the resinous gel-forming material is constructed in such a way as to produce air channels between the textile wrap and the part of the body immediately adjacent to the textile wrap. These air channels are designed as integral aspects of the construction of the device and are meant to provide spaces through which air can move while the textile wrap is worn. The air channels provide for increased air movement between the textile wrap and the skin. This increased air movement encourages additional evaporation of water from the surface of the textile wrap, thus enhancing the cooling effect.

BRIEF DESCRIPTION OF DRAWINGS

A preferred embodiment of the invention is illustrated in the accompanying drawings, in which.

DETAILED DESCRIPTION OF THE PREFERRED EMBODIMENT

The present invention provides, in a simple and convenient form, the means of furnishing cooling relief to the body during the pursuit of recreational activities. The present device is best suited to application to the forehead, although other configurations could apply to virtually any body location.

As shown in the accompanying drawings, this cooling compress comprises a textile holder 10, adapted to fit against the appropriate body pan of the individual wearer, in which a measured amount of dry particulate gel-forming resinous material 11 is held. In the unhydrated form, the textile holder 10, as assembled, is in the form of a flat, lightweight textile envelope 12. When the entire textile envelope 12 is immersed in water, the particulate gel-forming material 11 absorbs several hundred times its own weight in water and expands to fill the inner volume of the textile envelope 12.

Figure 1:
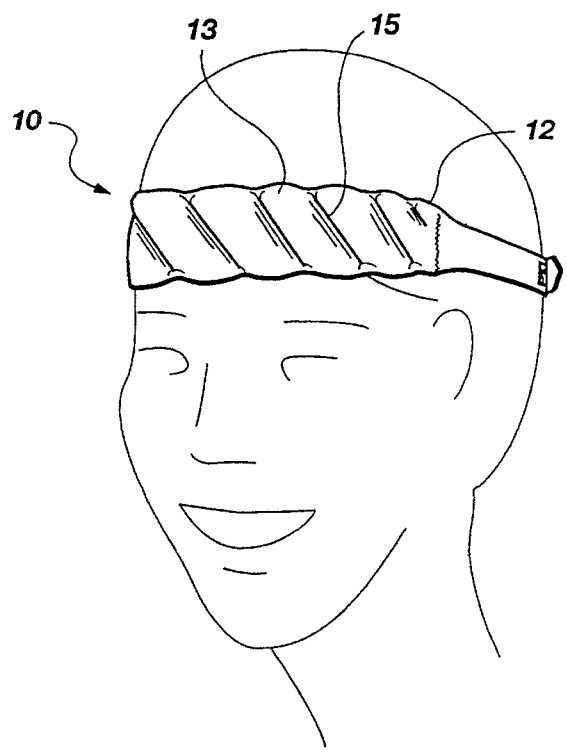
FIG. 1 is a front perspective view illustrating the textile wrap in its likely use orientation across the forehead of the user.

FIG. 1 illustrates the textile wrap or holder 10 as it might be worn when in use. While particular embodiments of the present invention are herein illustrated and described, it is not intended to limit the invention to such disclosures. Additional embodiments and configurations may also be made which provide for use of the device for additional purposes and to other areas of the body. The present device is constructed from a denim material, but could be constructed from any textile material suitable for the purpose.

Figure 2:
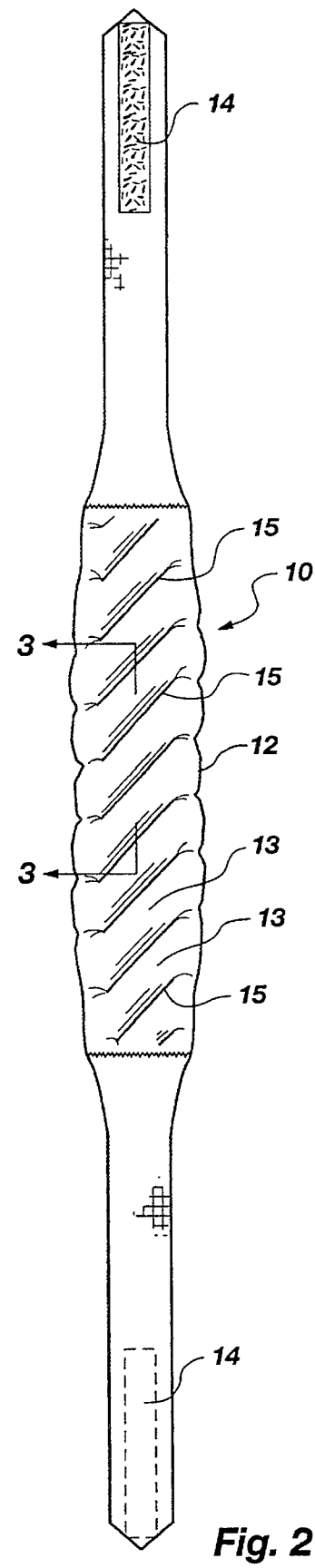
FIG. 2 is a top view of the textile wrap showing its general shape and construction, illustrating the assembled, hydrated device and the lateral seams sewn across the long axis of the tubular textile section, forming gel-filled segments.

FIG. 2 shows the assembled, hydrated holder 10. As shown, the invention consists of a tubular section of textile material forming a lightweight textile envelope 12. Lateral seams are sewn across the long axis of this envelope 12 which form the sediments 13 which are filled with the gel-forming resinous material 11. The device is shown using VELCRO® closures 14 to secure the invention in place. The device may also be tied or snapped to secure it in place. In normal use, the cooling compress is used in the hydrated condition. This hydration may be accomplished by immersing the entire textile envelope 12 in water and allowing the particulate resinous material to absorb water. The time required depends both on the particle size of the resinous material 11 as well as the temperature of the water. The hydration time is inversely proportional to the water temperature and directly proportional to the particle size. The textile envelope 12 is permeable to water and so does not restrict the flow of water into the inner volume of the envelope 12 where the particulate resinous material 11 is located. The textile envelope 12 then maintains a wicking action which slowly draws water from the interstices of the gel material 11 to the surface of the textile envelope 12. The water at the textile/air interface will then evaporate, providing a cooling effect over an extended period of time through evaporative cooling.

Several alternatives exist insofar as the construction of this device is concerned.

As mentioned, in filling the textile envelope with a pre-measured amount of particulate resinous gel-forming material 11, the gel material 11 may be either in the dry, unhydrated form, or alternatively, can be previously hydrated prior to addition to the textile envelope 12.

In using a continuous slab of resinous gel-forming material, the hydrated gel-forming material can be cut to the appropriate size and shape and the textile material sewn around it to form the envelope. Alternatively, it is also possible to sew the envelope around an appropriately sized piece of dry, unhydrated resinous gel-forming material.

Resinous gel-forming material which may be of use in the present invention can be prepared from a variety of starting materials including, but not restricted to:

Polyacrylamide

Anionic polyacrylamide

Polyvinyl alcohol

Maleic anhydride—vinylether copolymers

Poly(ethylene oxide)

Polyacrylic acid

Ethylene-maleic anhydride copolymers

Polyvinylether

Dextran

Polymethacrylic acid

Polyvinylsulfonic acid

Polystyrene sulfonic acid

Polyvinylamine

The present invention is not limited to the use of the starting materials listed here, but may include copolymers of one or more of either the materials mentioned, or other materials similar to these and suitable for forming a hydratable gel-like material. The preferred embodiment of the present invention is comprised from a group consisting of polymers, copolymers and terpolymers containing acrylic acid or acrylamide monomer moieties and most preferably, a polymer of acrylamide.

The mechanism by which the present invention provides the cooling relief is primarily through evaporative cooling. Water from the interstices of the hydrated gel-forming material is wicked to the surface of the textile envelope through the capillary action of the individual cloth fibers. The moisture thus wicked to the surface evaporates and results in a cooling sensation against the skin. While the degree of cooling is not suitable for therapeutic applications, it is effective in cooling the body during physical exertion accompanying recreational/leisure outdoor/indoor activities.

Figure 3:
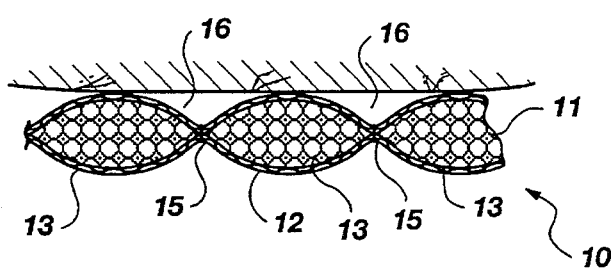
FIG. 3 is a transverse sectional view of the assembled, hydrated textile wrap in contact with the skin of the forehead or other body part, in which the hydrated gel segments are shown as well as the air channels.

As shown in FIG. 3, the textile envelope 12 can be constructed in such a way as to further enhance the cooling effect of the evaporation of water. The textile envelope 12 consists of a tubular section containing the resinous gel-forming material 11. Lateral seams 15 may be sewn into the textile envelope 12 as shown, which are approximately perpendicular to the long axis of the textile envelope 12. When the gel-forming material 11 is hydrated, the textile envelope 12 is transformed from a flat configuration to one which is comprised of numerous gel-filled segments 13. Each segment 13 is approximately cylindrical in shape, having a semi-spherical section which remains in contact with the skin during use. Each gel-filled segment 13 is separated by a cleavage which provides a channel 16 between the textile envelope and the skin. This channel 16 allows for the transport of air between the textile envelope 12 and the skin of the wearer. FIG. 3 illustrates the construction of the gel-filled segments 13 and their orientation to the skin when in the hydrated form. Also illustrated are the air channels 16 formed between the surface of the invention and the skin of the user of the device. The increased air flow thus achieved promotes additional evaporation of water at the air/textile envelope interface, thus enhancing the evaporative cooling effect.

The textile envelope 12 may be held in place using releasable fastening means such as Velcro 14 or tying the ends of the envelope in a suitable knot.

Thus, the present invention provides for a simple, convenient, easily constructed, reusable device which can provide for extended cooling relief when its user is engaged in outdoor or indoor physical activity.

While this invention has been described and illustrated herein with respect to preferred embodiments, it is understood that alternative embodiments and substantial equivalents are included within the scope of the invention as defined by the appended claims.

What is claimed is:

1. A device for provision of cooling relief to the body during physical recreational/leisure activity comprising: a reusable, flexible, water-permeable envelope structured to release water therethrough to effect evaporative cooling, said water-permeable envelope containing a particulate, water-hydratable, resinous, gel-forming material providing releasable water for evaporative cooling.

2. A device as set forth in claim 1, wherein said gel-forming material comprises a polymer of acrylamide.

3. A device as set forth in claim 1, wherein said gel-forming material is selected from a group consisting of polymers, copolymers and terpolymers containing acrylic acid and/or acrylamide moieties.

4. A device as set forth in claim 1, wherein said water-permeable envelope is structured to provide external air channels to enhance the evaporation of water to amplify the evaporative cooling effect.

5. A device as set forth in claim 1, wherein said water-permeable envelope is denim.

6. A device as set forth in claim 1, wherein said water-permeable envelope is structured with discrete, adjacent segments, and wherein said gel-forming material is uniformly distributed among said segments of said envelope.

7. A device for providing evaporative cooling to a body during physical activity comprising:

a reusable, flexible body having a closed interior space, said body being formed of water-permeable material for providing transport of water into and out of said closed interior space; and a particulate, resinous, water-hydratable material contained within said closed interior space, said water-hydratable material forming a gel upon absorption of water to provide water releasable through said water-permeable material to produce evaporative cooling.

* * * * *

UNITED STATES PATENT AND TRADEMARK OFFICE
CERTIFICATE OF CORRECTION

PATENT NO. : 5,597,577

DATED : 1/28/1997

INVENTOR(S) : Mathewson

It is certified that error appears in the above-indentified patent and that said Letters Patent is hereby corrected as shown below:

In Column 1, line 43, insert a comma after 3,545,230 and delete the period;

In Column 3, line 35, delete "pan" and insert --part-- therefor;

In Column 3, line 57, delete "sediments" and insert --segments-- therefor; and

In Column 4, line 24, delete the period after "dry".

Signed and Sealed this

Twenty-first Day of October 1997

Attest:

BRUCE LEHMAN

*Attesting Officer*  *Commissioner of Patents and Trademarks*